(12) United States Patent
Divi et al.

(10) Patent No.: US 10,399,926 B1
(45) Date of Patent: Sep. 3, 2019

(54) PROCESS FOR THE PREPARATION OF GABAPENTIN

(71) Applicant: Divi's Laboratories Ltd., Hyderabad (IN)

(72) Inventors: Satchandra Kiran Divi, Hyderabad (IN); Mysore AswathaNarayana Rao, Hyderabad (IN); Surendra Kalyan Nuthi, Hyderabad (IN)

(73) Assignee: Divi's Laboratories Ltd. (IN)

( * ) Notice: Subject to any disclaimer, the term of this patent is extended or adjusted under 35 U.S.C. 154(b) by 0 days.

(21) Appl. No.: 16/150,517

(22) Filed: Oct. 3, 2018

(30) Foreign Application Priority Data

Aug. 1, 2018 (IN) .............................. 201841028887

(51) Int. Cl.
*C07C 227/04* (2006.01)
*C07C 235/88* (2006.01)
*C07C 231/12* (2006.01)

(52) U.S. Cl.
CPC .......... *C07C 227/04* (2013.01); *C07C 231/12* (2013.01); *C07C 235/88* (2013.01); *C07C 2601/14* (2017.05)

(58) Field of Classification Search
CPC ... C07C 227/04; C07C 231/12; C07C 235/88; C07C 2601/14
See application file for complete search history.

(56) References Cited

U.S. PATENT DOCUMENTS 7,759,517 B2   7/2010   Villa et al.
2008/0097122 A1   4/2008   Villa et al.

FOREIGN PATENT DOCUMENTS

CN        105061239 A       11/2015

OTHER PUBLICATIONS

Thorpe, et al. The Formation and Reactions of Imino-compounds. Part XVIII. The Condensation of CycloHexaones with Cyanoacetamide Involving the Displacement of an AlkylGroup, J. Chem Soc., Trans. 1913, 103, 1586-1600.
International Search Report dated Apr. 24, 2019 of Application No. 18199836.0-1109.

*Primary Examiner* — Rosalynd A Keys
(74) *Attorney, Agent, or Firm* — Cesar Rivise, PC

(57) ABSTRACT

The present invention relates to an improved process for the preparation of Gabapentin. The process also relates to a new process for the preparation of 1, 1-cyclohexane diaceitic acid monoamide (CDMA), which is a key intermediate for the preparation of Gabapentin.

8 Claims, No Drawings

PROCESS FOR THE PREPARATION OF GABAPENTIN

FIELD OF INVENTION

The present invention relates to an improved process for the preparation of Gabapentin. The process also relates to a new process for the preparation of 1,1-cyclohexane diaceitic acid monoamide (CDMA), which is a key intermediate for the preparation of Gabapentin.

BACKGROUND OF THE INVENTION

Gabapentin is useful in treating epilepsy and various other cerebral disorders and is chemically 1-(amino methyl) cyclohexane acetic acid(I), having the structure shown below:

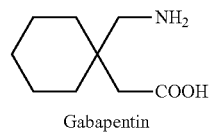

Gabapentin

Gabapentin was first disclosed by Warner-Lambert Co. in U.S. Pat. No. 4,024,175. A process for the preparation of gabapentin is described in U.S. Pat. No. 4,087,544 (Scheme 1). It involves converting cyclohexane diacetic acid (CDA, II) to its anhydride(III) followed by treatment with ammonia to give 1,1-cyclohexane diacetic acid monoamide (CDMA, IV). The CDMA (IV) is subjected to Hofmann reaction to obtain Gabapentin.

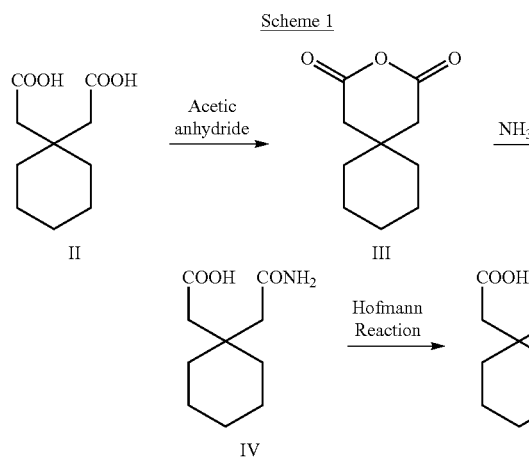

The required CDA (II) is prepared as described in U.S. Pat. No. 2,960,441 assigned to Warner-Lambert Co. The process involves Guareschi reaction between cyclohexanone and alkyl cyanoacetate in the presence of ammonia to obtain 2,4-dioxo-3-aza-spiro [5.5] undecane-1,5-dicarbonitrile (dinitrile, V) which on reaction with sulphuric acid undergoes hydrolysis and decarboxylation to give CDA (II, Scheme 2).

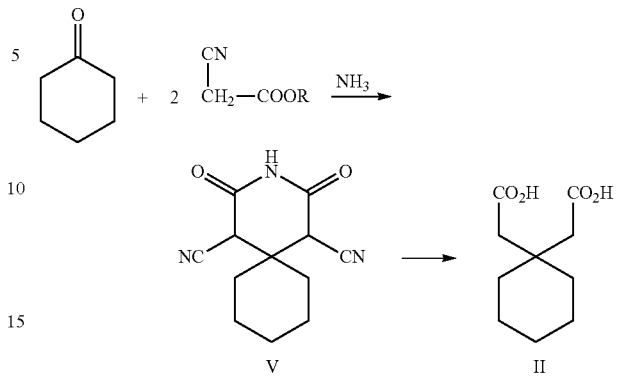

The process, especially the second step of converting dinitrile V to CDA (II), is very problematic. Firstly, the reaction requires the use of concentrated (95.6%) sulphuric acid and the reaction is carried out at 160° to 190° C. for several hours. During the decarboxylation reaction copious amount of carbon dioxide is liberated, resulting in frothing. The international patent application, WO 03/002504 also refers to the foaming problem faced during the decarboxylation step when carried out according to U.S. Pat. No. 2,960,441. The WO 03/002504 describes a slightly modified process involving two steps. In the first step, dinitrile V is reacted with 75 to 90% $H_2SO_4$ at 65° to 85° C. In the second step, the reaction mixture from the first step is reacted with 60 to 80% $H_2SO_4$ maintained at about 170° C. During the second step carbon dioxide liberation takes place. To avoid foaming, the addition is carried out slowly over a long period of time. But the process remains cumbersome, as it requires addition of a reaction mixture present in a 75-90% sulphuric acid solution to another sulphuric acid solution of 60-80% concentration at 170° C., while carbon dioxide gas is liberated.

Thorpe and Wood (J. Chem. Soc. 1913, 1586-1600) reported another method for the preparation of CDA (II) which involves reacting dinitrile V with sulphuric acid to obtain spiro[cyclohexane-1,9'-(3,7-diazabicyclo-[3.3.1]nonane)]-2',4',6',8'-tetraone (diimide, VI), which on further acid hydrolysis gives CDA (II, Scheme 3). However, no experimental details were given for the reactions.

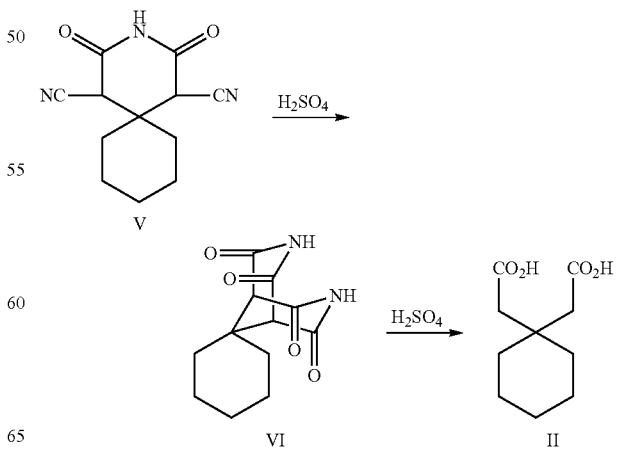

McElvain and Clemens (J. American Chemical Society, 1958, 80, 3915-3023) reported the synthesis of a number of related aromatic derivatives of diimides from the corresponding dinitriles and converting the diimides to corresponding diacids.

J. Med. Chem., 1998, 41, pg. 318-331, describes the preparation of diimide VI from dinitrile V by reacting with 60% sulphuric acid at a temperature of 120° to 140° C. for 10 to 15 minutes. However, the yield of the diimide VI obtained is only 40%. Earlier, U.S. Pat. No. 4,742,172 also reported the reaction under similar conditions.

Preparation of CDMA (IV) from dinitrile V, without going through CDA (II) as the intermediate, is reported in U.S. Pat. No. 7,759,517 (Scheme 4). Here, dinitrile is converted to diamide VII followed by sodium salt of diacid VIII. The diacid salt VIII is then converted to a monoimide IX followed by its hydrolysis to CDMA (IV).

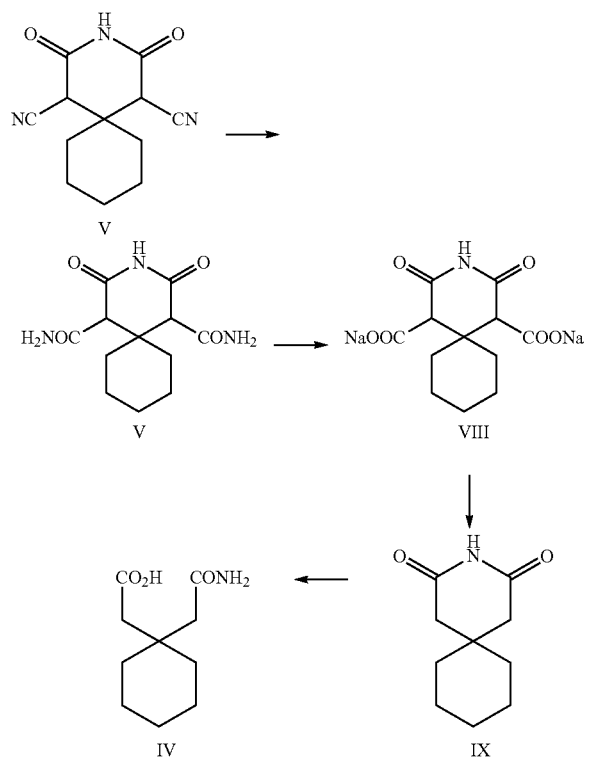

Thus there is a need for a better process which is environmentally safe and can be applied at industrial scale in a cost effective manner.

SUMMARY OF THE INVENTION

Our initial objective was to develop a process for the preparation of CDA(II), which is environmentally benign. Diimide VI was selected as the starting material, since it can be prepared without using concentrated sulphuric acid. The foaming problem is result of decarboxylation reaction under acidic conditions, it was envisaged that the foaming problem could be avoided by carrying out the reaction under alkaline conditions. Hence decarboxylation of diimide VI was explored under alkaline conditions, although such reaction is not reported in the prior art. We were pleasantly surprised to note that indeed the dimide VI underwent decarboxylation under alkaline conditions, free from any foaming. Further, even more surprisingly, hydrolysis of diimide VI under alkaline conditions resulted in CDMA(IV), which is a more advanced intermediate and can be converted in one step to Gabapentin (Scheme-5):

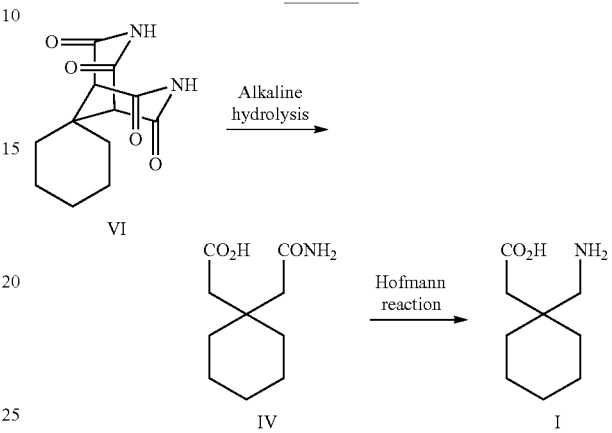

Thus, the present invention describes a new process for the preparation of CDMA(IV) from diimide VI under alkaline conditions, which on Hofmann reaction gives Gabapentin.

The present process is environmentally friendly as it uses dilute (50% to 70%) sulphuric acid instead of highly concentrated acid as reported in the prior art. The process is also free from foaming problems.

Furthermore, in the present process, CDMA (IV) is obtained directly without the need for preparing and isolating CDA (II) and its anhydride intermediate III, making the process more economical.

DETAILED DESCRIPTION OF THE INVENTION

The present invention provides a novel process for the preparation of gabapentin (I), comprising the steps of:
(a) reacting diimide VI with an alkali to produce CDMA (IV) and
(b) converting CDMA (IV) to gabapentin (I).

The starting material, diimide VI, can be prepared by the method described in J. Med. Chem. 1998, 41, pg. 318-331 and U.S. Pat. No. 4,742,172. It involves treating the dinitrile V with 60% sulphuric acid at a temperature of 120° to 140° C. for 10 to 15 minutes to obtain the diimide VI in 40% yields. The same method is described in U.S. Pat. No. 4,742,172, but does not mention the yields. Earlier, Thorpe and Wood (J. Chem. Soc. 1913, 1586-1600) had mentioned that the dinitrile V on reacting with concentrated sulphuric acid results in the diimide VI. They had not mentioned any details of the reaction conditions.

Since the reported yield (40%) is not satisfactory, the reaction was reinvestigated and studied in detail.

The study showed that the optimum concentration of sulphuric acid is between 50% to 70%. Below this concentration, the reaction is incomplete and at higher concentration, significant amount of diamide VII is formed as impurity. At >95% concentration, diamide VII is the major product.

The temperature also plays an important role. At the reported temperature of 120° to 140° C., a mixture of diimide VI and CDA (II) is obtained. The optimum temperature for the reaction is in the range of about 90° C. to 110° C. Below about 80° C., the reaction is incomplete. Thus, under the optimum conditions, diimide VI is obtained in about 80% yield, which is double the yield compared to prior art report.

The diimide VI undergoes base catalyzed decarboxylation and hydrolysis to give CDMA (IV) in about 80% yield having purity of >99%.

The reaction can be carried out by heating the diimide VI with an aqueous solution of an alkali base. The alkali solution can have strength of 5% to 50%, preferably 15% to 25% (w/v). Although most experiments were conducted using sodium hydroxide as the base, other alkali bases such as potassium hydroxide, lithium hydroxide, sodium tert-butoxide and potassium tert-butoxide also gave similar results. Heating can be conveniently carried out at reflux temperature (100-105° C.). At lower temperatures of about 70° C. to 80° C., conversion is slow and the reaction is incomplete.

Duration of the reaction plays a significant role on the yields and purity of the product CDMA(IV). When the reaction is carried out using 20% solution of sodium hydroxide at reflux temperature for about 20 hours, CDMA (IV) is obtained in about 80% yields having a purity of >99% (HPLC). At shorter duration, the product gets contaminated with monoimide IX as the major impurity. At about 5 hours, monoimide IX is obtained as the major product, while CDMA (IV) is the minor product. At about 24 hours, slight amount (1-2%) of CDA(II) formation is observed.

After the reaction, the reaction mixture is cooled, diluted with water and pH adjusted to about 4 by addition of acid. During the adjustment of pH, some amount of carbon dioxide gas liberation is observed. But this does not result in the frothing of the reaction medium and can be easily regulated by adjusting rate of addition of acid. Filtering the solids and washing with little cold water gives pure CDMA (IV).

The CDMA (IV) can then be converted into Gabapentin by several processes, including the process developed earlier by the present assignee as described in U.S. Pat. No. 8,431,739.

Thus, the present process is simple and does not use any organic solvents. It eliminates the use of highly concentrated sulphuric acid. Another advantage of the present process is that, carbon dioxide is liberated only during the neutralization of the alkaline reaction mixture at room temperature. This does not result in foaming and frothing unlike in the Warner-Lambert process (U.S. Pat. No. 4,024,175) where heavy frothing occurs when carbon dioxide is liberated during heating of the reaction mixture containing sulphuric acid at 170° C.

The present process is also more economical as the more advanced intermediate, CDMA (IV), is obtained directly from the dinitrile V without going through the steps of CDA (II) and its anhydride intermediate III.

The embodiments of the present invention are illustrated in the following examples, which are not intended in any way to limit the scope of the invention. One skilled in the art can modify the details to suit the inputs and desired outcomes without affecting the present invention.

EXAMPLES

Chemical purity was determined using HPLC under the following conditions:

Column: X-Terra RP C18, 150×4.6 mm, 5 μm

Mobile phase: Buffer: Acetonitrile (760:240); flow rate: 1.0 ml/min

Buffer preparation: 0.58 g of monobasic ammonium phosphate and 1.83 g of sodium perchlorate in 1.0 lit of water adjust with perchloric acid to a pH 1.8.

Column Temperature: 40° C., Detection: 215 nm

Example 1: Preparation of Spiro [cyclohexane-1, 9'-(3, 7-diazabicyclo-[3.3.1] nonane)]-2', 4', 6',8'-tetraone (VI)

120 mL of 60% solution of sulphuric acid was heated to 70°-75° C. and to this solution was added 2, 4-dioxo-3-aza-spiro [5.5] undecane-1, 5-dicarbonitrile (V) (30.0 g, 0.129 moles) slowly. After the addition, the reaction mixture was heated to 100° C.-105° C. and maintained at this temperature for 22 hours. The reaction mixture was cooled, diluted with 180 mL water and stirred for 1 hour. The solids were filtered, washed with water and dried at 60° C. for 5 hours to obtain spiro[cyclohexane-1, 9'-(3, 7-diazabicycle-[3.3.1] nonane)]-2', 4', 6', 8'-tetraone (VI), 27 g (Yield: 83.3%). Melting Range (DSC): 406.88-410.96° C. (Lit: 400-405° C.; J. Chem. Soc., 1911, 99, 422-448). IR(KBr): 3209, 3097 (—NH stretch), 2948, 2850 (C—H Stretch, 1708 (C=O), 1425& 1363 cm$^{-1}$. $^1$H NMR (300 MHz, DMSO): δ 11.67 (s, 2H, —NH), 3.75 (s, 2H) & 1.39-1.48 (m, 10H, cyclohexyl group). $^{13}$C NMR (75 MHz, DMSO): δ 166.60 (4×C=O), 57.19 (2×CH), 37.69 (CR$_4$), 20.74, 25.33 & 31.84 (cyclohexyl group). MS: m/z: 249.22 (M-1). Purity by HPLC: 98.23%.

Example 2: Preparation of Spiro [cyclohexane-1, 9'-(3, 7-diazabicyclo-[3.3.1] nonane)]-2', 4', 6', 8'-tetraone (VI)

Experiment was conducted as described in Example 1, but instead of using 60% solution of sulphuric acid, 70% solution of sulphuric acid was used. Yield: 78.7%, HPLC: 96.8%.

Example 3: Preparation of Spiro [cyclohexane-1, 9'-(3, 7-diazabicyclo-[3.3.1] nonane)]-2', 4', 6', 8'-tetraone (VI)

Experiment was conducted as described in Example 1, but instead of carrying out the reaction at 100° to 105° C., the reaction was carried out at 90° to 95° C. Yield: 77.1%, HPLC: 98.27%.

Example 4: Preparation of 1, 1-cyclohexane Diacetic Acid Monoamide (CDMA, IV)

To 36 mL of solution of 20% sodium hydroxide was added di-imide VI, (15.0 g, 0.0599 moles) and refluxed (100-105° C.) for 18 hours. The reaction mixture was cooled, diluted with 400 mL water, further chilled to 5°-10° C., the pH of the solution was adjusted to about 4.0 with concentrated hydrochloric acid and stirred for 30 minutes. The solids were filtered, washed with water and dried at 55° C. for 1 hour to obtain 1,1-cyclohexane diacetic acid monoamide IV, 9.65 g (Yield: 80.8%). Melting Range: 145.6-146.8° C. (Lit.: 141-146° C., https://www.sigmaaldrich.com/catalog). IR (KBr): 3400, 2932, 1717 (C=O), 1653 &1591 cm$^{-1}$. $^1$H NMR (300 MHz, DMSO): δ 12.45 (s, 1H, —COOH), 7.02-7.44 (s, 2H, —CONH$_2$), 2.40 (s, 2H), 2.23 (s, 2H) & 1.36-1.41 (m, 10H, cyclohexyl group). $^{13}$C NMR (75 MHz, DMSO): δ 174.28, 173.41 (2×C=O), 42.55, 42.26 (2×-C$\underline{H}_2$), 35.28 (CR$_4$), 35.08, 26.02 &21.48 (cyclohexyl group). MS: m/z: 200.08 (M+1). Purity by HPLC: 99.68%. (Monoimide IX: 0.21%; CDA (II): 0.06%).

Example 5: Preparation of 1, 1-cyclohexane Diacetic Acid Monoamide (CDMA, IV)

Experiment was conducted as described in Example 4, but instead of using 20% solution (w/v) of sodium hydroxide, 40% solution was used. Yield: 81.7%, HPLC: 99.01%.

Example 6: Preparation of 1, 1-cyclohexane Diacetic Acid Monoamide (CDMA, IV)

Experiment was conducted as described in Example 4, but using 20% solution of potassium hydroxide in place of 20% solution of sodium hydroxide. Yield: 77.7%, HPLC: 96.5%.

Example 7: Preparation of 1, 1-cyclohexane Diacetic Acid Monoamide (CDMA, IV)

Experiment was conducted as described in Example 4, but instead of refluxing the reaction for 18 hours, the reaction was refluxed for 15 hours. Yield: 80.4%, HPLC: 96.3%; 1.5% monoimide IX.

Example 8: Reference Example: Preparation of Gabapentin (I)

CDMA (IV) was treated with a solution of sodium hypochlorite in an alkaline medium and converted into gabapentin as described in the U.S. Pat. No. 8,431,739.

We claim:

1. A process for the preparation of gabapentin comprising the steps of:
   a) reacting spiro[cyclohexane-1,9'-(3,7-diazabicyclo-[3.3.1]nonane)]-2',4',6',8'-tetraone of the formula VI:

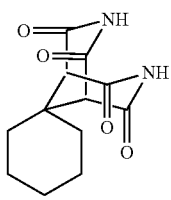

VI with an alkali to obtain 1,1-cyclohexane diacetic acid monoamide of the formula IV and

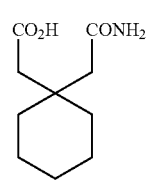

IV b) converting the compound IV obtained in step-a to gabapentin I by Hofmann reaction using alkali hypo halite.

2. The process as claimed in claim 1, wherein at step-a, the alkali used is selected from the group consisting of sodium hydroxide, potassium hydroxide, lithium hydroxide, sodium tert-butoxide and potassium tert-butoxide.

3. The process as claimed in claim 2, wherein the alkali is sodium hydroxide.

4. The process as claimed in claim 3, wherein the concentration of the alkali is in the range of 5% to 50% (w/v).

5. The process as claimed in claim 3, wherein the concentration of the alkali is in the range of 15% to 25% (w/v).

6. The process as claimed in claim 1, wherein at step-a, the reaction is carried out at reflux temperature for a time period of 6 to 24 hours.

7. The process as claimed in claim 6, wherein at step-a, the reaction is carried out for a time period of 15 hours to 20 hours.

8. The process as claimed in claim 1, wherein the compound of the formula VI used in step-a is prepared by reacting 2,4-dioxo-3-aza-spiro[5.5]undecane-1,5-dicarbonitrile of the formula V

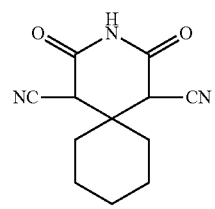

V with 50% to 70% solution of sulfuric acid at 90° C. to 110° C.

* * * * *